United States Patent
Van Brunt et al.

(10) Patent No.: US 10,335,570 B2
(45) Date of Patent: Jul. 2, 2019

(54) METHOD OF SEPARATING AND DISTRIBUTING OXYGEN

(71) Applicant: Vbox, Incorporated, White Bear Lake, MN (US)

(72) Inventors: Nicholas P. Van Brunt, White Bear Lake, MN (US); Theodore W. Jagger, White Bear Lake, MN (US); Perry B. Lonnes, White Bear Lake, MN (US); John A. Kivisto, Oak Grove, MN (US)

(73) Assignee: 3B MEDICAL INC., Winter Haven, FL (US)

( * ) Notice: Subject to any disclaimer, the term of this patent is extended or adjusted under 35 U.S.C. 154(b) by 252 days.

(21) Appl. No.: 14/187,908

(22) Filed: Feb. 24, 2014

(65) Prior Publication Data

US 2014/0166003 A1    Jun. 19, 2014

Related U.S. Application Data

(62) Division of application No. 12/839,979, filed on Jul. 20, 2010, now Pat. No. 8,695,600.

(51) Int. Cl.
*A61M 16/10* (2006.01)
*B01D 53/053* (2006.01)
(Continued)

(52) U.S. Cl.
CPC ...... *A61M 16/101* (2014.02); *A61M 16/0003* (2014.02); *A61M 16/0051* (2013.01);
(Continued)

(58) Field of Classification Search
CPC ............ A61M 16/101; A61M 16/0051; A61M 16/20; A61M 16/0672; A61M 16/0057;
(Continued)

(56) References Cited

U.S. PATENT DOCUMENTS 3,121,625 A    2/1964  Broughton
3,142,547 A *  7/1964  Skarstrom ............ B01D 53/047
                                                        95/100

(Continued)

FOREIGN PATENT DOCUMENTS

EP    368649 A1    5/1990
EP    760247 A2    3/1997
(Continued)

OTHER PUBLICATIONS

Recommendations of the Fifth Oxygen Consensus Conference, 1999.
(Continued)

*Primary Examiner* — Tan-Uyen T Ho
*Assistant Examiner* — Margaret M Luarca
(74) *Attorney, Agent, or Firm* — Carlson, Gaskey & Olds, P.C.

(57) ABSTRACT

Disclosed is a method of providing oxygen rich gas. Oxygen is separated from ambient air with an oxygen separator in discrete pulses, one pulse at a time. The start of the pulse is synchronized with the beginning of an inhalation of a person. The oxygen rich gas in each pulse is separated from the ambient air in real time during a nitrogen adsorption step concurrent with each inhalation.

10 Claims, 4 Drawing Sheets

(51) Int. Cl.
- *B01D 53/047* (2006.01)
- *A61M 16/00* (2006.01)
- *A61M 16/06* (2006.01)
- *A61M 16/20* (2006.01)

(52) U.S. Cl.
CPC .... *A61M 16/0057* (2013.01); *A61M 16/0672* (2014.02); *A61M 16/10* (2013.01); *A61M 16/20* (2013.01); *B01D 53/0476* (2013.01); *B01D 53/053* (2013.01); *B01D 2256/12* (2013.01); *B01D 2257/102* (2013.01); *B01D 2258/00* (2013.01); *B01D 2259/402* (2013.01); *B01D 2259/4533* (2013.01); *B01D 2259/4541* (2013.01)

(58) Field of Classification Search
CPC ............. A61M 16/0003; A61M 16/10; B01D 53/0476; B01D 53/053; B01D 2256/12; B01D 2259/402; B01D 2259/4541; B01D 2259/4533; B01D 2257/102
USPC ............. 128/202.26, 204.22, 205.12, 205.27
See application file for complete search history.

(56) References Cited

U.S. PATENT DOCUMENTS

| | | |
|---|---|---|
| 3,236,028 A | 2/1966 | Rutan |
| 3,717,974 A | 2/1973 | Batta |
| 3,880,616 A | 4/1975 | Myers et al. |
| 3,922,149 A | 11/1975 | Ruder et al. |
| 4,169,715 A | 10/1979 | Eriksson |
| 4,194,890 A | 3/1980 | McCombs et al. |
| 4,222,750 A | 9/1980 | Gauthier et al. |
| 4,263,018 A * | 4/1981 | McCombs ........... B01D 53/047 95/19 |
| 4,354,859 A | 10/1982 | Keller, II et al. |
| 4,386,945 A | 6/1983 | Gardner |
| 4,448,592 A | 5/1984 | Linde |
| 4,449,990 A | 5/1984 | Tedford, Jr. |
| 4,472,177 A | 9/1984 | Sircar |
| 4,491,459 A | 1/1985 | Pinderton |
| 4,502,873 A | 3/1985 | Mottram et al. |
| 4,576,616 A | 3/1986 | Mottram et al. |
| 4,627,860 A | 12/1986 | Rowland |
| 4,648,395 A | 3/1987 | Sato et al. |
| 4,648,888 A | 3/1987 | Rowland |
| 4,673,415 A | 6/1987 | Stanford |
| 4,681,099 A | 7/1987 | Sato et al. |
| 4,684,377 A | 8/1987 | Haruna et al. |
| 4,702,903 A | 10/1987 | Keefer |
| 4,801,308 A | 1/1989 | Keefer |
| 4,802,899 A | 2/1989 | Vrana et al. |
| 4,813,977 A | 3/1989 | Schmidt et al. |
| 4,816,121 A | 3/1989 | Keefer |
| 4,826,510 A | 5/1989 | McCombs |
| 4,880,443 A | 11/1989 | Miller et al. |
| 4,892,566 A | 1/1990 | Bansal et al. |
| 4,925,464 A | 5/1990 | Rabenau et al. |
| 4,948,401 A | 8/1990 | Izumi et al. |
| 4,968,329 A | 11/1990 | Keefer |
| 4,971,609 A | 11/1990 | Pawlos |
| 4,973,339 A | 11/1990 | Bansal |
| 5,002,591 A | 3/1991 | Stanford |
| 5,034,023 A | 7/1991 | Thompson |
| 5,069,688 A | 12/1991 | Wells |
| 5,071,449 A | 12/1991 | Sircar |
| 5,082,473 A | 1/1992 | Keefer |
| 5,084,075 A | 1/1992 | Sircar |
| 5,096,469 A | 3/1992 | Keefer |
| 5,112,367 A | 5/1992 | Hill |
| 5,114,440 A | 5/1992 | Reiss |
| 5,169,506 A | 12/1992 | Michaels |
| 5,186,793 A | 2/1993 | Michaels |
| 5,228,840 A | 7/1993 | Swank |
| 5,247,826 A | 9/1993 | Frola et al. |
| 5,256,172 A | 10/1993 | Keefer |
| 5,268,021 A | 12/1993 | Hill et al. |
| 5,340,381 A | 8/1994 | Vorih |
| 5,366,541 A | 11/1994 | Hill et al. |
| 5,370,112 A | 12/1994 | Perkins |
| 5,415,683 A | 5/1995 | Leavitt |
| 5,429,666 A | 7/1995 | Agrawal et al. |
| RE35,099 E | 11/1995 | Hill |
| 5,469,372 A | 11/1995 | McBrearty et al. |
| 5,474,595 A | 12/1995 | McCombs |
| 5,487,775 A | 1/1996 | LaCava et al. |
| 5,531,807 A | 7/1996 | McCombs |
| 5,565,018 A | 10/1996 | Baksh et al. |
| 5,578,115 A | 11/1996 | Cole |
| 5,593,478 A | 1/1997 | Hill et al. |
| 5,656,066 A | 8/1997 | Reiss et al. |
| 5,672,195 A | 9/1997 | Moreau et al. |
| 5,711,787 A | 1/1998 | Neill et al. |
| 5,730,778 A | 3/1998 | Hill et al. |
| 5,762,686 A | 6/1998 | Borzio |
| 5,772,737 A | 6/1998 | Andreani et al. |
| 5,814,130 A | 9/1998 | Lemcoff et al. |
| 5,814,131 A | 9/1998 | Lemcoff et al. |
| 5,820,656 A | 10/1998 | Lemcoff et al. |
| 5,827,358 A | 10/1998 | Kulish et al. |
| 5,846,294 A * | 12/1998 | Doong ............... B01D 53/053 95/98 |
| 5,858,062 A | 1/1999 | McCulloh et al. |
| 5,871,564 A | 2/1999 | McCombs |
| 5,891,217 A | 4/1999 | Lemcoff et al. |
| 5,893,275 A | 4/1999 | Henry |
| 5,893,944 A | 4/1999 | Dong |
| 5,906,672 A | 5/1999 | Michaels et al. |
| 5,917,135 A | 6/1999 | Michaels et al. |
| 5,928,189 A | 7/1999 | Phillips et al. |
| 5,931,159 A | 8/1999 | Suzuki et al. |
| 5,935,297 A | 8/1999 | Amlinger |
| 5,948,142 A | 9/1999 | Holmes et al. |
| 5,968,236 A | 10/1999 | Bassine |
| 5,979,440 A | 11/1999 | Honkonen et al. |
| 5,985,001 A | 11/1999 | Garrett et al. |
| 5,985,113 A | 11/1999 | Crome et al. |
| 5,988,165 A | 11/1999 | Richet, II et al. |
| 5,997,611 A | 12/1999 | Doong et al. |
| 5,997,617 A | 12/1999 | Czabala et al. |
| 6,010,555 A | 1/2000 | Smolarek et al. |
| 6,017,315 A | 1/2000 | Starr et al. |
| 6,030,435 A | 2/2000 | Monereau et al. |
| 6,033,457 A | 3/2000 | Lawless |
| 6,051,050 A | 4/2000 | Keefer et al. |
| 6,056,804 A | 5/2000 | Keefer et al. |
| 6,068,680 A | 5/2000 | Kulish et al. |
| 6,146,447 A | 11/2000 | Sircar et al. |
| 6,152,134 A | 11/2000 | Webber et al. |
| 6,162,283 A | 12/2000 | Conrad et al. |
| 6,171,371 B1 | 1/2001 | Derive et al. |
| 6,176,897 B1 | 1/2001 | Keefer |
| 6,212,904 B1 | 4/2001 | Arkharov et al. |
| 6,217,635 B1 | 4/2001 | Conrad et al. |
| 6,287,366 B1 | 9/2001 | Derive et al. |
| 6,290,759 B1 | 9/2001 | Fenner et al. |
| 6,302,107 B1 | 10/2001 | Richer, II et al. |
| 6,311,719 B1 | 11/2001 | Hill et al. |
| 6,314,957 B1 | 11/2001 | Boissin et al. |
| 6,344,069 B2 | 2/2002 | Smolarek et al. |
| 6,346,139 B1 | 2/2002 | Czabala |
| 6,372,026 B1 | 4/2002 | Takemasa et al. |
| 6,446,630 B1 | 9/2002 | Todd, Jr. |
| 6,457,485 B2 | 10/2002 | Hill et al. |
| 6,461,410 B1 | 10/2002 | Abe et al. |
| 6,471,744 B1 | 10/2002 | Hill |
| 6,478,850 B1 | 11/2002 | Warren |
| 6,478,857 B2 | 11/2002 | Czabala |
| 6,511,526 B2 | 1/2003 | Jagger et al. |
| 6,520,176 B1 | 2/2003 | Dubois et al. |
| 6,524,370 B2 | 2/2003 | Maheshwary et al. |
| 6,544,318 B2 | 4/2003 | Dee et al. |
| 6,547,851 B2 | 4/2003 | Warren |

(56) References Cited

U.S. PATENT DOCUMENTS

| | | | |
|---|---|---|---|
| 6,551,384 B1 | 4/2003 | Ackley et al. |
| 6,629,525 B2 | 10/2003 | Hill et al. |
| 6,641,644 B2 | 11/2003 | Jagger et al. |
| 6,641,645 B1 | 11/2003 | Lee et al. |
| 6,651,653 B1 | 11/2003 | Honkonen et al. |
| 6,651,658 B1 | 11/2003 | Hill et al. |
| 6,687,164 B2 | 1/2004 | Honkonen et al. |
| 6,691,702 B2 | 2/2004 | Appel et al. |
| 6,698,423 B1 | 3/2004 | Honkonen et al. |
| 6,712,087 B2 | 3/2004 | Hill et al. |
| 6,712,886 B2 | 3/2004 | Kim |
| 6,764,534 B2 | 7/2004 | McCombs et al. |
| 6,793,719 B2 | 9/2004 | Kim et al. |
| 6,802,889 B2 | 10/2004 | Graham et al. |
| 6,805,729 B2 | 10/2004 | Lim et al. |
| 6,811,590 B2 | 11/2004 | Lee et al. |
| 6,824,590 B2 | 11/2004 | Dee et al. |
| 6,866,041 B2 | 3/2005 | Hardy, Jr. et al. |
| 6,866,950 B2 | 3/2005 | Connor et al. |
| 6,878,186 B2 | 4/2005 | Neary |
| 6,908,503 B2 | 6/2005 | McCombs et al. |
| 6,935,460 B2 | 8/2005 | McCombs et al. |
| 6,949,133 B2 | 9/2005 | McCombs et al. |
| 6,953,498 B2 | 10/2005 | Walker et al. |
| 6,959,728 B2 | 11/2005 | McCombs et al. |
| 7,011,092 B2 | 3/2006 | McCombs et al. |
| 7,025,329 B2 | 4/2006 | Winter |
| 7,066,985 B2 | 6/2006 | Deane et al. |
| 7,105,038 B2 | 9/2006 | Lee et al. |
| 7,135,059 B2 | 11/2006 | Deane et al. |
| 7,156,903 B2 | 1/2007 | McCombs |
| 7,171,963 B2 | 2/2007 | Jagger et al. |
| 7,279,029 B2 | 10/2007 | Oochialini et al. |
| 7,291,271 B2 | 11/2007 | Galbraith |
| 7,329,304 B2 | 2/2008 | Bliss et al. |
| 7,350,521 B2 | 4/2008 | Whitley et al. |
| 7,368,005 B2 | 5/2008 | Bliss et al. |
| 7,402,193 B2 | 7/2008 | Bliss et al. |
| 7,431,032 B2 | 10/2008 | Jagger et al. |
| 7,438,745 B2 | 10/2008 | Deane et al. |
| 7,445,663 B1 | 11/2008 | Hunter et al. |
| 7,455,717 B2 | 11/2008 | Sprinkle |
| 7,491,040 B2 | 2/2009 | McCombs et al. |
| 7,510,601 B2 | 3/2009 | Whiley et al. |
| 7,517,385 B2 | 4/2009 | Winter |
| 7,533,872 B2 | 5/2009 | Lee et al. |
| 7,585,351 B2 | 9/2009 | Deane et al. |
| 7,604,004 B2 | 10/2009 | Jagger et al. |
| 7,604,005 B2 | 10/2009 | Jagger et al. |
| 7,686,870 B1 | 3/2010 | Deane et al. |
| 7,708,802 B1 | 5/2010 | Deane et al. |
| 7,713,421 B2 | 5/2010 | Galbraith |
| 7,722,698 B2 | 5/2010 | Thompson et al. |
| 7,722,700 B2 | 5/2010 | Sprinkle |
| 7,730,887 B2 | 6/2010 | Deane et al. |
| 7,753,996 B1 | 7/2010 | Deane et al. |
| 7,758,672 B2 | 7/2010 | Lee et al. |
| 7,766,010 B2 | 8/2010 | Jagger et al. |
| 7,780,768 B2 | 8/2010 | Taylor et al. |
| 7,794,522 B2 | 9/2010 | Bliss et al. |
| 7,866,315 B2 | 1/2011 | Jagger et al. |
| 2003/0005928 A1 | 1/2003 | Appel et al. |
| 2003/0167924 A1 | 9/2003 | McCombs et al. |
| 2004/0103894 A1 | 6/2004 | Loncar |
| 2005/0072426 A1 | 4/2005 | Deane et al. |
| 2006/0174871 A1* | 8/2006 | Jagger et al. ............ 128/201.21 |
| 2006/0174875 A1 | 8/2006 | Jagger et al. |
| 2006/0174877 A1 | 8/2006 | Jagger et al. |
| 2006/0174880 A1 | 8/2006 | Jagger et al. |
| 2006/0174881 A1 | 8/2006 | Jagger et al. |
| 2006/0283325 A1 | 12/2006 | Sugano |
| 2007/0039466 A1* | 2/2007 | Nawata ................. A61M 16/10 95/96 |
| 2007/0056583 A1 | 3/2007 | Jagger et al. |
| 2007/0056584 A1 | 3/2007 | Jagger et al. |
| 2009/0065007 A1* | 3/2009 | Wilkinson et al. ...... 128/205.27 |
| 2011/0017216 A1 | 1/2011 | Van Brunt et al. |

FOREIGN PATENT DOCUMENTS

| | | |
|---|---|---|
| EP | 860646 A2 | 8/1998 |
| EP | 0873776 A2 | 10/1998 |
| EP | 1125623 A1 | 8/2001 |
| GB | 2174922 A | 11/1986 |
| WO | 9857727 A1 | 12/1998 |
| WO | 9858219 A1 | 12/1998 |
| WO | 9943416 A1 | 9/1999 |
| WO | 9943418 A1 | 9/1999 |
| WO | 3092817 A1 | 11/2003 |

OTHER PUBLICATIONS

"AirSep lowers boom", www.hmenews.com/2004.12/depts/vendors/vendors1.htm.

Peter L Bliss, Robert W McCoy, Alexander B Adams, A Bench Study Comparison of Demand Oxygen Delivery Systems and Continuous Flow Oxygen, Respiratory Care, Aug. 1999, vol. 44. No. 8.

* cited by examiner

METHOD OF SEPARATING AND DISTRIBUTING OXYGEN

CROSS-REFERENCE TO RELATED APPLICATION(S)

This application claims priority as a divisional application under 35 U.S.C. § 121 of earlier filed U.S. patent application Ser. No. 12/839,979, entitled "METHOD OF SEPARATING AND DISTRIBUTING OXYGEN" and filed on Jul. 20, 2010, which is hereby incorporated by reference.

BACKGROUND

The present disclosure relates to an adsorption based gas separation apparatus that separates oxygen from ambient air with beneficial improvements over the prior art in size, weight and energy consumed per unit of oxygen separated from air.

Pressure swing separation systems are known to offer the best energy efficiency for oxygen separation at small production rates. Systems using the Skarstrom PSA cycle (described in *Pressure Swing Adsorption* by Douglas M. Ruthven et al., John Wiley & Sons, Inc., 1994, hereinby incorporated by reference, Section 3.2.1) for medical oxygen production are common examples of these small scale systems and are familiar to those skilled in the art. These systems are known to consume about 350 watts of electrical power to produce about 5 liters per minute of oxygen with about 90% purity.

The portable concentrators are battery powered to eliminate tethering utility cords and similar power supply structures attached to the apparatus. Research efforts were directed toward energy efficiency of the separation process. As previously noted, pressure swing separation systems are known to offer the best energy efficiency for oxygen separation at small production rates. Prior art oxygen separators were measured, and the performance and behavior of one of these commonly used systems was analyzed—the currently popular Invacare model IRC5LX (specifications available from www.invacare.com). In this device, an electrically driven pneumatic compressor cycled air from 1 to 3 atmospheres pressure, following the Skarstrom cycle steps, through two columnar containers of adsorbent having high adsorption capacity for nitrogen and other polar molecules. By measuring the pneumatic power of the pumped gas stream including the power associated with the adiabatic heating of the pumped gas and comparing that to the electrical power input to the pump, it was determined that much energy was being lost to pump inefficiency. This finding was set aside, and research was focused on exploring the power consumption aspects of the separation cycle steps.

There is a specific amount of theoretical power associated with pumping a stream of gas through a given pressure difference as is required to operate a pressure swing separation system. For example: (1 Liters/Minute flow rate)×(1 Atmosphere pressure rise)=0.592 watts of power. Adiabatic heating of this gas stream consumes additional power in watts. Reducing the pressure change or the flow rate of the pumped gas stream needed to drive the separation cycle steps would therefore directly reduce the power required to produce a given amount of oxygen. Research and testing was done to determine the minimum pump pressure and flow rates to produce a given oxygen separation rate.

SUMMARY

Disclosed is a method of providing oxygen rich gas. Oxygen is separated from ambient air with an oxygen separator in discrete pulses, one pulse at a time. The start of the pulse is synchronized with the beginning of an inhalation of a person. The oxygen rich gas in each pulse is separated from the ambient air in real time during a nitrogen adsporition step concurrent with each inhalation.

In another embodiment, a delivery system for oxygen separated from ambient air is disclosed. The delivery system has a separator with at least one separation column, the separation column containing an inlet at a first end and an outlet at a second end, a buffer column having a single inlet at a first end, a vacuum pump, and a valve system that connects the vacuum pump with the separation column. The delivery system also has a nose cannula. The oxygen separator is capable of separating oxygen from air in discrete pulses in response to inhalation by a person through the nose cannula.

In yet another embodiment, a delivery system for oxygen separated from ambient air is disclosed. The delivery system has a separator with at least one separation column, the separation column containing an inlet at a first end and an outlet at a second end, a buffer column having a single inlet at a first end, a vacuum pump, and a valve system that connects the vacuum pump with the separation column and connects the separation column and buffer column. The delivery system also has a nose cannula. The oxygen separator is capable of separating oxygen from air in discrete pulses in response to inhalation by a person through the nose cannula, and the oxygen separator utilizes the buffer column containing the single inlet on the first end of the column for controlling flow in and out of the buffer column, functioning as a last in/first out (LIFO) buffer for the purity of a separated gas flowing in and out of the inlet port.

DETAILED DESCRIPTION

The separation apparatus described herein was developed for use in an oxygen concentrator that provides portable supplementary oxygen to patients with lowered blood oxygen levels. The concentrator is much lighter, smaller and more energy efficient than prior art devices, and is small enough so that the apparatus can be conveniently worn by a patient as they move about rather than wheeled on a cart or carried like a piece of luggage. The separation components contributed directly to the unique portability features of the concentrator. The apparatus can be scaled in size for higher or lower oxygen separation rates using the unique design features to provide reduced size, weight and power benefits for other applications. Configurations that used one, two and three adsorption columns all using the same separation cycle steps were built and tested.

Figure 1:
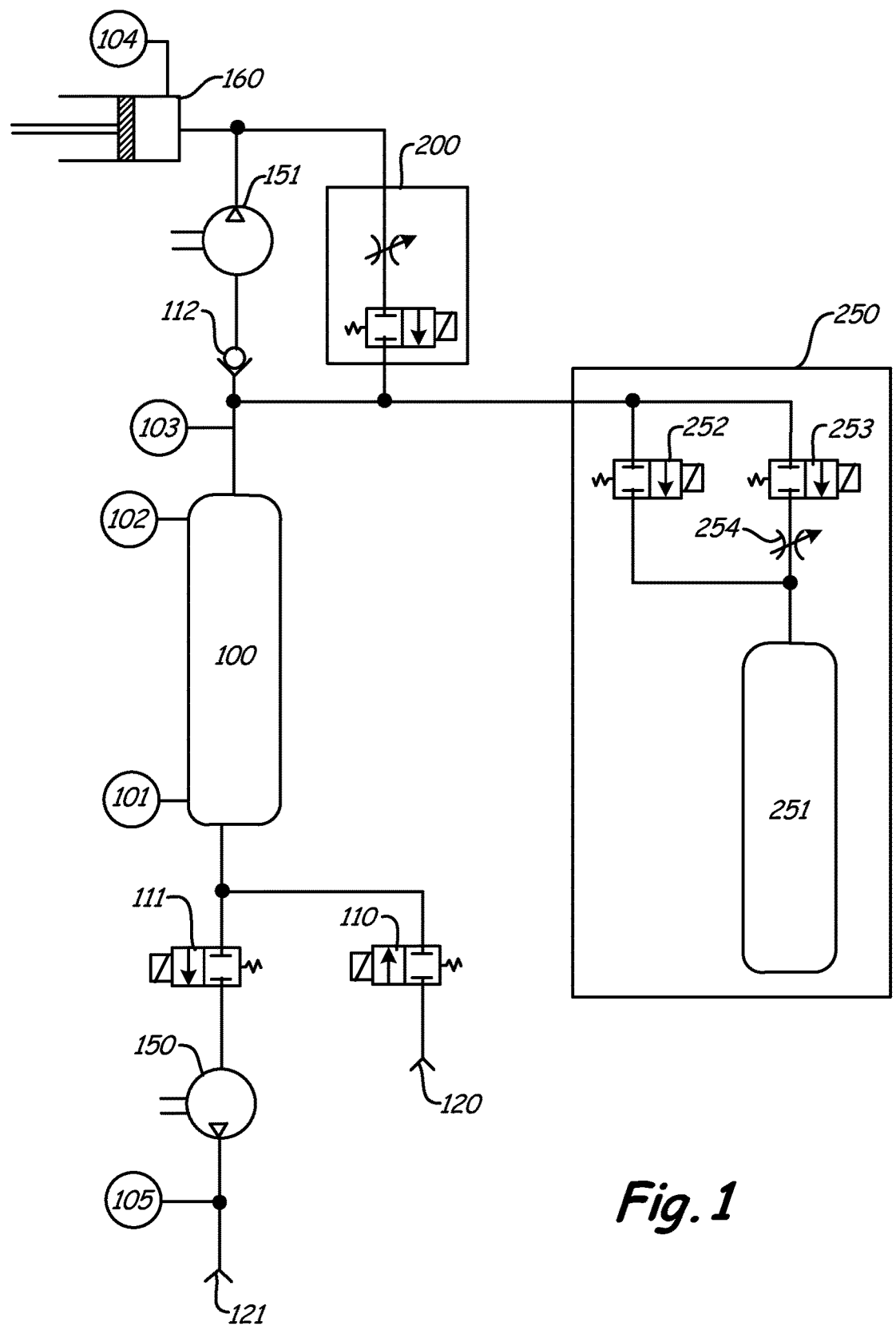
FIG. 1 is a schematic view of an oxygen separator utilizing a single adsorption column.

Research began by exploring the minimum pump pressure and flow rates with a simple form of pressure swing separation system. The physical model in FIG. 1 was constructed and connected instrumentation to accurately measure gas pressures, flow rates and compositions as it cycled through a sequence of separation steps. In FIG. 1, 100 is a 1 inch (2.54 cm) diameter by 4 inch (10.16 cm) long cylinder (or column) packed with adsorbent beads. Ambient air at approximately 1 atmosphere (101 kPa) can flow into 100 at the feed end adjacent monitoring point 101 by way of solenoid valve 110 from port 120. Waste gas can be pumped from 100 at feed end 101 through valve 111 by vacuum pump 150 and vented to atmosphere through port 121. A gas stream reduced in nitrogen can be pumped from 100 at product end 102 through check valve 112 by pump 151 and transferred to accumulator 160. The components in boxes 200 and 250 were not present during these first tests. Monitoring points 101 through 105 are locales where instrumentation was attached to monitor pressure, flow, and composition of the gas streams as the gas streams varied during cycle steps. Customized instrumentation was developed that had a pressure response time of less than 1 millisecond, a flow rate response time of 10 milliseconds, and a composition response time of less than 750 milliseconds. The customized instrumentation fed a digital storage oscilloscope that could capture time variant measures of the parameters. The instrumentation proved crucial to measuring and understanding the detailed behavior of the experimental configurations.

Figure 2:
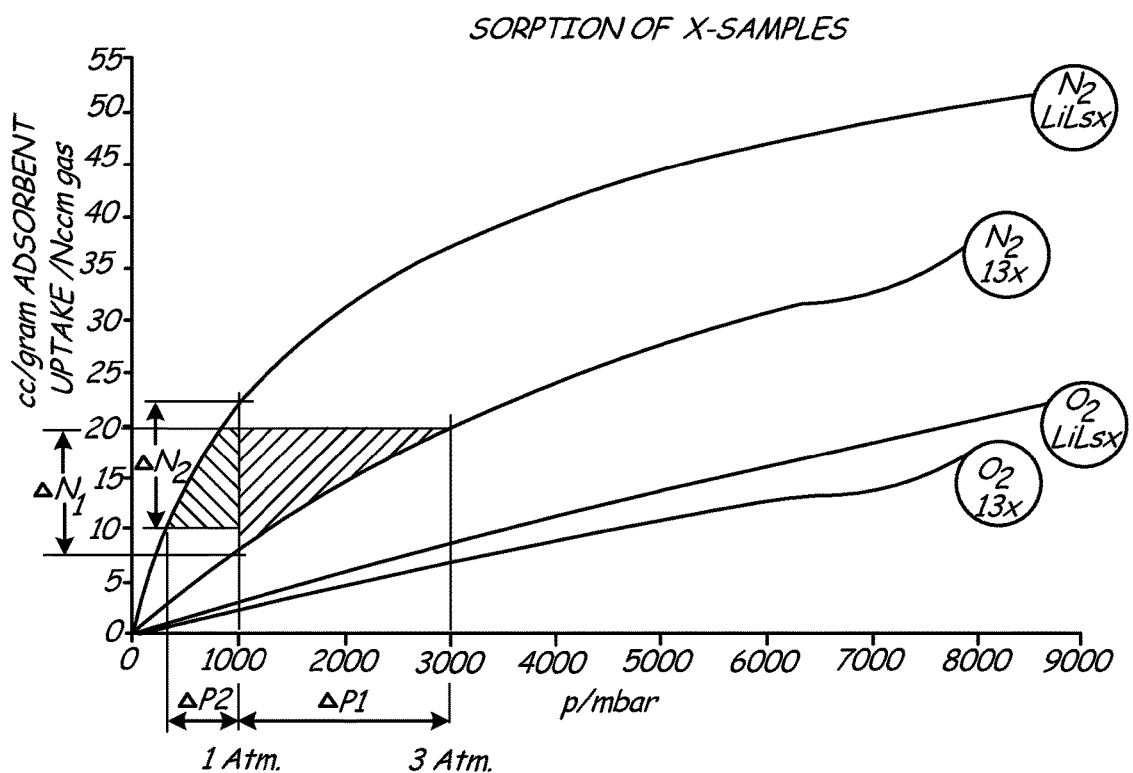
FIG. 2 is a graph of the isotherms of two adsorbents.

The adsorbent materials useful for oxygen separation have an adsorption capacity for nitrogen that is higher than the adsorption capacity for oxygen over a pressure range of several atmospheres. These adsorbent materials are characterized by their isotherms. Isotherms are graphs showing the amount of gas contained in a given mass of adsorbent material as a function of pressure at a fixed temperature. The isotherms for nitrogen and oxygen are of primary interest. Air is nearly 1% argon. The argon isotherms for these adsorbents are nearly identical to the oxygen isotherms so the separation steps discussed here relate to oxygen and argon as though they were the same. These isotherms for two different adsorbents are shown in FIG. 2.

The type 13× adsorbent is commonly used in small oxygen concentrators such as the Invacare device that was tested. Another available adsorbent type is LiLSX. Isotherms of LiLSX are plotted in FIG. 2 with the 13× isotherms for comparison. As shown in FIG. 2, the ratio of nitrogen capacity to oxygen capacity is much higher for the LiLSX than the 13× at 2 atmospheres pressure and below. The difference of the adsorbents is even more pronounced at 1 atmosphere and below where the absolute nitrogen capacity of the LiLSX is seen to be much higher than the 13× while the oxygen capacities are similar between the two.

Thus, it was determined that using the LiLSX adsorbent could provide energy savings over adsorbents such as 13× with lesser nitrogen to oxygen capacity ratios. Any pressure driven oxygen separation sequence for separating oxygen from air must include the minimum steps of increasing the pressure of an air stream while passing it through the adsorbent to adsorb nitrogen, followed by decreasing the pressure to desorb the nitrogen from the adsorbent and carry it away in a waste gas stream. The amount of oxygen that can be separated from the air stream in one cycle increases with increased amounts of nitrogen that can be adsorbed from that air stream. The nitrogen isotherms indicate the amount of nitrogen that is adsorbed for a given pressure change. The higher the slope of the nitrogen isotherm curve, the less pressure change is required to change the amount of nitrogen adsorbed by a given mass of adsorbent. In FIG. 2, to change the amount of nitrogen held in a mass of 13× adsorbent by the amount N1, a pressure change P1 is required. With the LiLSX adsorbent, an amount of nitrogen N2 in the figure required pressure change P2. N2 is approximately equal to N1, but P2 is only about ⅓ the pressure change of P1.

In a portable concentrator, pump 151 is providing the pneumatic power to produce this pressure change. As described, pressure difference across the pump linearly affects the pumping power input. Operating over a pressure range that spans a steep segment of the nitrogen isotherm could allow a given volume of nitrogen to be cyclically adsorbed and desorbed with relatively less power provided by the pump. In FIG. 2, the oxygen isotherms for the two adsorbents are more similar but the 13× oxygen isotherm shows much more oxygen being adsorbed over the larger P1 pressure range than the LiLSX oxygen isotherm over the smaller P2 pressure range. More oxygen will be adsorbed during the high pressure nitrogen adsorbing steps using the 13× adsorbent than in the low pressure steps using the LiLSX adsorbent. The adsorbed oxygen subtracts directly from the amount of product oxygen that can be produced. Using these two effects in combination, more oxygen should be produced from the same amount of nitrogen pumped over a smaller pressure range in a system using the LiLSX adsorbent than from one using 13×. Utilizing LiLSX adsorbent in a portable concentrator system will greatly reduce the pneumatic energy required to separate a given volume of oxygen.

The behavior of the LiLSX adsorbent (OXYSIV MDX from UOP LLC) was explored in the steep section of its nitrogen isotherm in pressure ranges from 1 atmosphere (101 kPa) and below using the simplified test system of FIG. 1 without blocks 200 or 250. The system is commonly referred to as a vacuum swing type system. The initial cycle steps considered were:

1. Evacuate the column 100 through the feed end adjacent point 101 to a vacuum level V measured by a pressure sensor at point 102.
2. Pressurize the column to 1 atmosphere with air through the feed end.
3. Feed air through the feed end at near 1 atmosphere pressure at a constant flow rate while pumping oxygen rich gas out the product end 102 into the accumulator 160.

The process is similar to the vacuum swing cycle from Ruthven et al., Section 3.2.4. An abrupt increase in the gas flow rate from the product end of the column measured by a flow sensor at point 103 during step 3 marked the completion of nitrogen adsorption in the column and the end of step 3. At that point in time, the entire column was at equilibrium with atmospheric nitrogen partial pressure of about 0.78 atmospheres (79 kPa) and oxygen (including about 1% argon) at 0.22 atmospheres (22 kPa). The cycle repeats with step 1 resetting the nitrogen equilibrium in the column to a lower level according to the end vacuum level V. The low oxygen partial pressure throughout the entire column at the end of step 3 left very little oxygen to be lost to the waste stream during step 1.

By measuring the performance of this test system, how vacuum level V affected the ratio of power consumed to oxygen produced by this cycle was determined. Rather than considering the oxygen produced, the system was viewed as nitrogen eliminated from the product stream. As the vacuum level V in step 1 was decreased (absolute pressure lowered) the amount of nitrogen removed from the product stream during step 3 increased at an increasing rate for each additional decrement of V as predicted by the nonlinear increasing slope of the nitrogen isotherm. Oxygen adsorption also occurred according to the oxygen isotherm. Oxygen was then lost in the waste stream during step 1 as it was desorbed during the evacuation of the column. However, the oxygen isotherm is nearly linear so there was a linear increase in the amount of lost oxygen with decreased V while the amount of nitrogen removed increased at an increasing rate. Stronger end vacuums therefore increased oxygen produced, due to larger volumes of adsorbed nitrogen, at an increasing rate.

Another important performance factor is the purity of the product oxygen stream and how it was affected by V. Industry standards required a design to produce oxygen with a purity of 86% or higher. The product purity increased with reduced V (stronger vacuum). Thus, the evacuate step 1 had to reduce the nitrogen partial pressure in the column to less than 0.08 atmosphere (8.1 kPa) to produce the necessary oxygen purity from the feed step 3 that would follow.

Strong vacuums, including those below 0.1 atmosphere (10 kPa) present problems when considering the practical characteristics of vacuum pumps. The volumetric efficiency of positive displacement vacuum pumps decreases in proportion to the vacuum level being pumped. For example, at 0.1 atmospheres (10 kPa) an ideal pump is only capable of 10% of its volumetric pumping capacity. In practice, even this greatly reduced capacity cannot be realized due to some small volume remaining in the displacement space at the end of a compression stroke in the pump. For example, if this remaining volume were greater than 10% of the pump displacement stroke the pump would have entirely stopped pumping before reaching the 0.1 atmosphere (10 kPa) end vacuum. Because of this problem, requirements for oxygen purity and production rates could not be satisfied with an existing vacuum pump small enough to be compatible with portability goals if the pump had to operate at low vacuum. The evacuate step took so much of the cycle time as it approached the low end vacuum V that the resulting oxygen production rate became too slow.

Experiments with modifications to these simple separation steps were performed, trying to obtain a result that could produce 86% oxygen purity with weaker (higher pressure) vacuum levels. The product oxygen has a very low nitrogen partial pressure. Feeding the product oxygen into the product end of the column during pressurize step 2 instead of air into the feed end should lower the equilibrium pressure for nitrogen in the product end causing nitrogen to be desorbed from the product end and swept toward the feed end of the column. No nitrogen is removed from the column by this step because the feed end is closed. Nitrogen is just reorganized leaving less nitrogen adsorbed toward the product end and more toward the feed end. During the feed step that follows, more of the nitrogen in the product gas stream will be adsorbed as it passes through the product end of the column due to the nitrogen equilibrium having been set to a lower pressure by the oxygen pressurization. Higher product purity is obtained.

The aforementioned step was added to the test apparatus by adding the components and connections in box 200 of FIG. 1. Testing proved that oxygen could then be produced with the desired purity using an end vacuum level as high as 0.3 atmospheres (30 kPa). The column was being evacuated to 0.3 atmospheres (30 kPa) much faster than it was able to evacuate to the original 0.1 atmospheres (10 kPa). A more practical vacuum pump with a weaker end vacuum could now be used to power the cycle. However, significant additional time was now being spent due to a longer feed step that recycled the oxygen used to pressurize the column back into the product oxygen accumulator. The oxygen was being passed between accumulator 160 and the column in steps 2 and 3 consuming extra cycle time. The system increased product oxygen purity but did not produce additional oxygen product. The effective oxygen production rate was reduced. Further experimentation revealed that by only partially pressurized the column to about 0.6 atmospheres (61 kPa) with product oxygen through block 200 followed by rapidly pressurizing of the column the rest of the way to 1 atmosphere (101 kPa) with air at the feed end through valve 110, the system produces the same amount of oxygen and purity as with total pressurization by oxygen. The modified system saves time in the cycle with less pressurization oxygen to be passed between the accumulator and the column.

The system with the improved version of the cycle was tested with the addition of product oxygen fed into the product end of the column while the column was being evacuated through the feed end. The addition of product oxygen into the feed end is done in the prior art to improve product purity in pressure swing (above 1 atmosphere (101 kPa)) systems using the Skarstrom cycle. When the improved system was tested, no beneficial results were discerned. From the results, the following were postulated: When a stream of air was fed through the modified adsorbent column previously equilibrated at a lower partial pressure for nitrogen according to the level of V, a sharp dividing line called the mass transfer zone (MTZ) developed and propagated through the column in the direction of gas flow. The MTZ was undetectable by the test setup and the attached instrumentation. The MTZ sharply segregated the gas compositions in the column with the feed air gas composition on the feed side of the zone and the product gas composition on the product side of the zone. The nitrogen was being adsorbed within the narrow MTZ leaving the gas down stream of the MTZ partially stripped of nitrogen. Unfortunately, the process could not be performed in reverse with the same distinct segregation between the gas compositions. In the reverse process, oxygen rich product gas would be fed into the product end of the column while evacuating nitrogen rich gas out the feed end. The reverse process did cause a mass transfer as nitrogen was desorbed from the column, but the mass transfer was not confined to a narrow zone. The reverse mass transfer zone was broadly dispersed throughout the column and immeasurable as a result of the shape and nonlinearity of the nitrogen isotherm curve compared to the oxygen isotherm (Ruthven et al., Section 2.4.1). With no narrow zone separating the product oxygen from the nitrogen rich gas in the column, the oxygen is diffusing and much of the oxygen is swept to the feed end by the nitrogen rich gas flow and is lost to the waste stream during the evacuation step. The loss of product oxygen was determined to likely be offsetting any possible gains in the amount or purity of product oxygen being separated in the tested system.

The use of this last process step was abandoned. The result was a process that separated product oxygen with adequate purity within a relatively small absolute pressure range of 0.3 to 1 atmosphere. This would significantly reduce pumping power over that of typical pressure swing cycles operating in a higher pressure span well above 1 atmosphere. By running the feed step until the mass transfer zone was close to breakthrough at the product end of the column, little product oxygen in the column is left to be lost during the evacuation step. These factors produced the most product oxygen volume from the feed step for the volume of gas pumped from the column during the evacuate step. Minimizing both the pressure range and the volume of gas to be pumped for a given amount of oxygen produced, in this way, required a uniquely small amount of pneumatic power from the pump to drive the separation steps.

Figure 3:
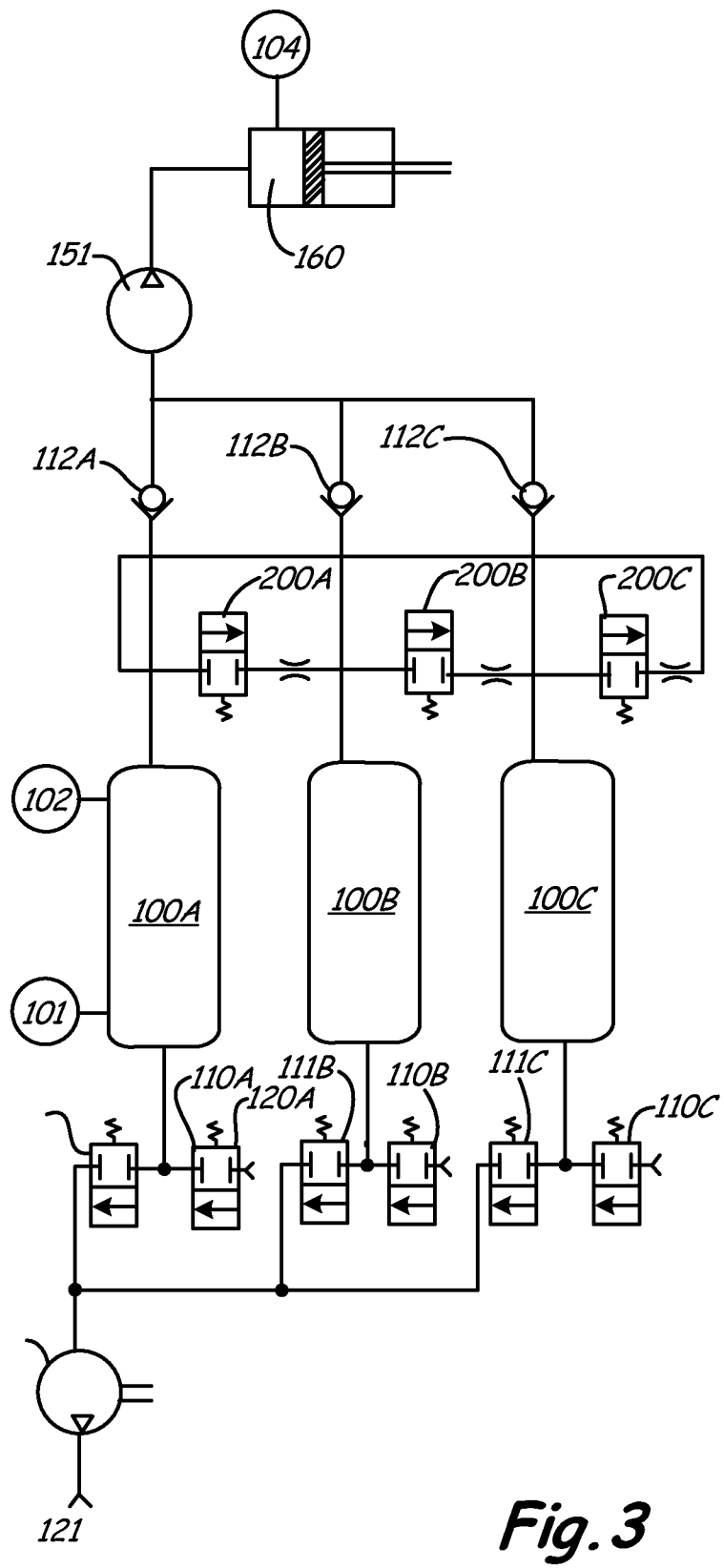
FIG. 3 is a schematic view of an oxygen separator utilizing three identical adsorption columns.

Another apparatus, shown in FIG. 3, was built to test physical scale implementations of the aforementioned separation cycle. In FIG. 3 the components 100 through 200 are included and perform the same steps in the same way as in FIG. 1 copied three times labeled 100A-100C through 200A-200C. The cycle steps were grouped into a sequence of three equal time intervals forming a three phase cycle. The first phase evacuated the column from 1 atmosphere (101 kPa) to 0.3 atmospheres (30 kPa) through the feed end. The second phase pressurized the column to 0.6 atmospheres (61 kPa) with product oxygen through the product end, and then pressurized the column to 1 atmosphere (101 kPa) with air through the feed end. The third phase fed air at 1 atmosphere (101 kPa) through the feed end and vented product oxygen from the product end. Three columns were connected with tubing, valves and a vacuum pump so that each column cycled through these three phases. Each column was offset in time from the other two by one phase step. This way, at any instant in time, there was always one column being evacuated allowing the pump to run continuously allowing full use of the available pumping capacity. One column was always venting product oxygen providing a somewhat continuous oxygen stream. The configuration was implemented and tested for oxygen production volume and purity with a variety of different valve schemes. Sequencer controlled electric solenoid valves, motor driven rotary valves, and pressure driven poppet valves in various combinations were tested. All tested valves worked to produce the desired cycle steps, but there was a reduction in the purity and quantity of product oxygen produced by one of the examples. Determining the cause of the reduced performance in the one flawed version led to the eventual understanding of the problem, which led to an important improvement in the cycle steps.

During the pressurize phase for each column, oxygen was fed into the product end of that column bringing the pressure to about 0.6 atmosphere (61 kPa). The oxygen was being produced by one of the other two columns during its feed phase offset in time to be concurrent with the column being pressurized. For example, column 100A in its feed phase would pass oxygen to 100B in its concurrent pressurize phase to pressurize it through 200A. Roughly half of the oxygen volume transferred from the column in the feed phase is used to pressurize the other column. The remaining half of the oxygen from the column in the feed phase is removed as product by pump 151 through the check valves into the accumulator 160. The earliest half of the oxygen stream out of the feed column was used to pressurize the other column. These and the single column in FIG. 1 all performed well. However, due to a small difference in its valve scheme, the poorly performing implementation happened to be using the last half of this oxygen stream rather than the first half to pressurize the other column. The later part of the stream was slightly less pure than the first part. This seemingly small difference was determined to be the cause of the significant performance reduction of that implementation. Correcting this to use the first half of the product stream for pressurization eliminated the performance deficit thus proving the effect.

As disclosed, the system was able to beneficially increase the end pressure of the evacuate step and still maintain purity of the product by partially pressurizing the evacuated column with product oxygen. The partial pressure of nitrogen in the product end of the column after the phase 2 pressurization steps sets the partial pressure for nitrogen in the beginning of the phase 3 oxygen stream due to equilibrium between the gas stream and the adsorbent. Nitrogen is adsorbed in the column as the product stream flows and some of the nitrogen is being adsorbed in the product end. As nitrogen is adsorbed the equilibrium point for nitrogen in the product stream moves toward progressively higher partial pressures causing a gradual rise in the nitrogen content of the product stream above the initial level as the feed progresses toward breakthrough of the mass transfer zone. Establishing a lower equilibrium level for nitrogen at the product end of the column therefore lowers the nitrogen level of the entire product stream due to its lower initial level. This is set by the nitrogen partial pressure of the last pressurizing gas to pass through the product end of the column being pressurized. The first part of the oxygen rich stream out of that column during the next feed step therefore has the least nitrogen and the last out has the most. When used to pressurize a column, for best performance, the more pure first oxygen out of the feeding column should be the last gas into the column being pressurized. That means the product gas stream should be buffered and its entire composition order reversed before being used to pressurize a column. The configurations that had worked best during tests did not reverse the entire order of the gas stream, but at least was a step in the right direction since the system used the first approximate half of the product stream to pressurize rather than the last half as with the configuration that performed poorly.

A way to implement a last in first out buffer for the product gas was discovered that could be used to perform the order reversal. An additional column filled with LiLSX adsorbent having only a single port at one end was utilized. As gas flowed into this buffer column, oxygen was least adsorbed and traveled the farthest down the column. Nitrogen was strongly adsorbed and was captured by the adsorbent closest to the inlet. As gas was removed from this column, the nitrogen close to the inlet (now acting as an outlet) flowed out early due to its proximity to the outlet and the desorbing effect of the lower nitrogen content gas flowing behind it from farther into the column. The benefit of this last in/first out (LIFO) gas buffer was tested on the separation cycle by first integrating the LIFO into the earlier single column test apparatus of FIG. 1. Block 200 was removed from FIG. 1 and replaced it with block 250. This includes LIFO column 251 equal in volume to separation column 100. Also, valve 252 provided a controllable connection between the LIFO and the product end 102 of the separation column 100.

The test apparatus was modified to revisit and more thoroughly explore different combinations of product gas feed rates, timing, and pressures fed into the product end of the column during the evacuate step. It was expected that there should be some (probably small) amount of product oxygen gas that, if controlled carefully, should also help reduce the partial pressure of nitrogen toward the product end of the column before the oxygen in that gas had time to diffuse to the feed end and be wasted during evacuate. This was tested through variable flow restrictor 254 with timing controlled by valve 253 linking the product end of 100 to the LIFO 251.

The test apparatus valves were controlled to performed the following sequence of steps:
1. Begin evacuating the column through the feed end 101.
2. At an adjustable evacuate pressure threshold, measured at 102, begin an adjustable low flow rate of product oxygen into the product end 102 from the LIFO 251 through valve 253 and restrictor 254.

3. Stop evacuating and continue to flow product oxygen more rapidly by opening valve 252 from the LIFO into the product end pressurizing the column to an adjustable level measured at 102.

4. Finish pressurizing the column with air through the feed end 101 to ambient atmosphere.

5. Feed air into the feed end of the column 101 through 110 while pulling oxygen out of the product end 102 to refill the LIFO 251 through 252 until it is at 1 atmosphere pressure.

6. Continue feeding air and removing product oxygen from the product end of the column through 112 and pump 151 into the accumulator 160 until the mass transfer zone is near breakthrough.

A process to discover the best combination of pressure, flow, and timing settings during steps 2 and 3 was performed. The best combination was found to include a very low oxygen flow rate into the product end of the column from the LIFO during only the last part of the evacuate step. The specific flows and pressures are specific to the size and shape of the separation column and need to be found experimentally for different column geometries.

The first gas out of the LIFO that fed into the product end of the column toward the end of evacuate during step 2 had the highest nitrogen content. The last gas out of the LIFO entered the column at the end of the pressurization during step 3 and had the lowest nitrogen content. This resulted in the column, at the end of pressurization step 4, continuously ordered with nitrogen partial pressure equilibriums highest at the feed end of the column and very low at the product end. Oxygen partial pressures were ordered in the opposite direction so the sum of the two partial pressures was 1 atmosphere (101 kPa) throughout the column. With this, oxygen purity 86% and higher were obtained with end vacuums as high as 0.5 atmospheres (51 kPa). This is a vacuum swing of only 0.5 atmospheres (51 kPa) compared to a pressure swing of 2 atmospheres (203 kPa) for the typical Skarstrom PSA cycle. A very significant reduction in pneumatic power resulted. Also, the relatively weak vacuums can be achieved rapidly by a smaller and more practical vacuum pump thus shortening the evacuate step and the total cycle time for a given amount of oxygen produced.

Figure 4:
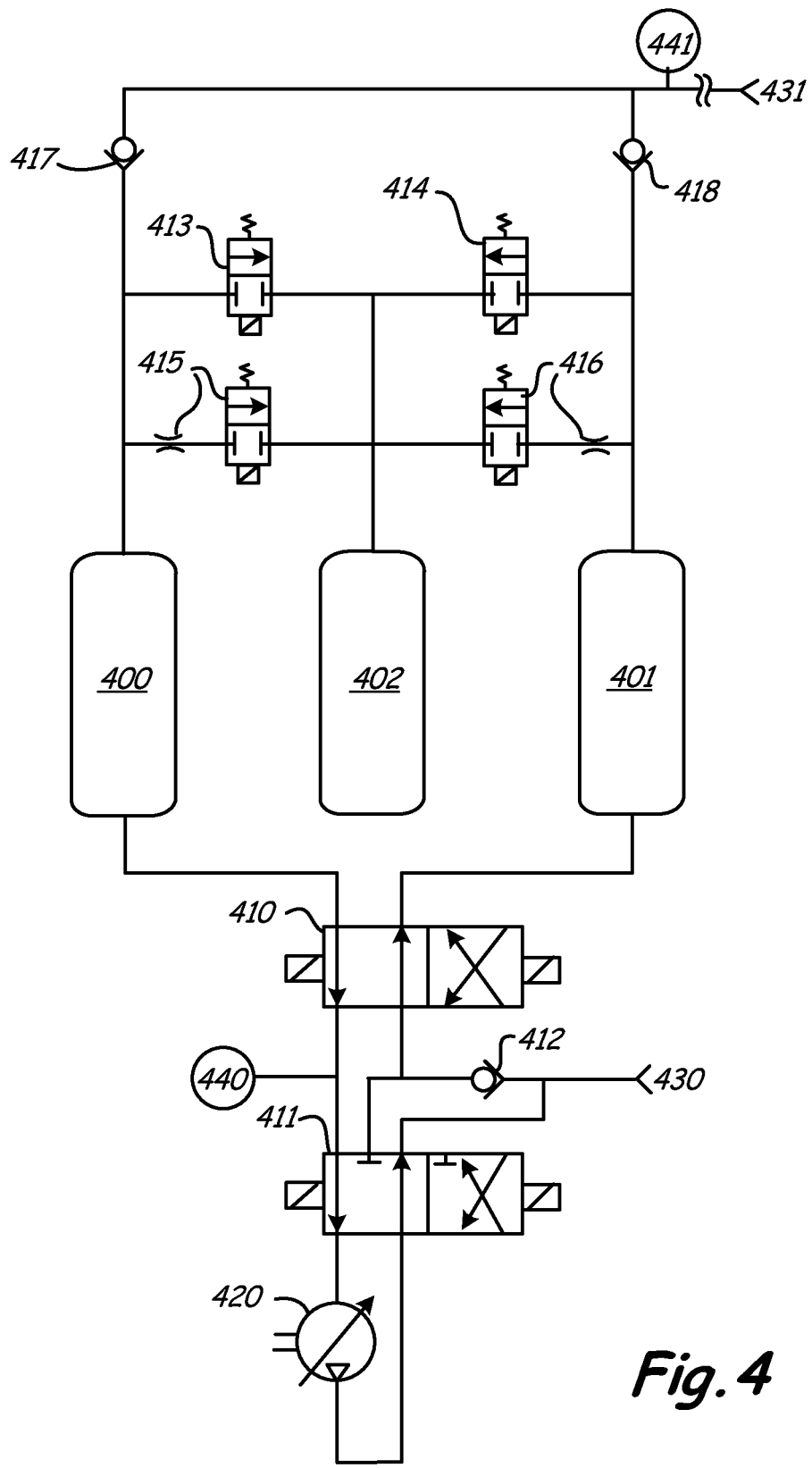
FIG. 4 is a schematic view of an oxygen separator utilizing two adsorption columns with a last in/first out buffer column.

Using these separation cycle steps, the design shown in FIG. 4 was constructed for a portable oxygen concentrator. The portable system is configured with two separation columns 400 and 401 to allow some overlapping of concurrent cycle steps, and one LIFO buffer 402 that was shared during the cycle steps occurring in the two columns.

In FIG. 4 cycle step 1 is first performed on column 400. With valves 410 and 411 positioned as illustrated, variable rate vacuum pump 420 evacuates column 400 from the feed end pulling gas through valves 410 and 411 then passing the gas from pump 420 back through valve 411 as shown and out port 430 to atmosphere. Valves 413, 415, and 417 are closed.

Step 2 begins on column 400 when the vacuum level in column 400 reaches a selected threshold measured at monitoring point 440. Valve with flow restrictor 415 is opened to establish a controlled flow of oxygen rich gas from the LIFO 402 into the product end of column 400 while the evacuation of column 400 that began in step 1 continues. Step 2 is ended after a selected amount of time.

Step 3 begins on column 400 with valve 411 switched to the opposite state halting evacuate of column 400. Valve 413 is opened allowing a more rapid flow of oxygen from the LIFO 402 into column 400 pressurizing it to about 0.6 atmospheres (61 kPa).

Step 4 begins with valve 410 switched to the opposite state providing a path for ambient air through port 430, check valve 412 and valve 410 into the feed end of column 400 pressurizing it to 1 atmosphere (101 kPa). Valves 413, 415, and 417 are all closed during step 4.

Step 5 refills LIFO 402, which was left at a partial vacuum after transferring gas to pressurize column 400 in step 3. Valve 413 is opened drawing oxygen rich gas from column 400 into LIFO 402 until it reaches 1 atmosphere (101 kPa). Column 400 remains at 1 atmosphere (101 kPa) throughout this step with the path to its feed end still open to ambient air as in step 4. All activity is stopped after step 5 waiting for a patient with a nose cannula (not illustrated) connected to port 431 to begin a breath inhalation.

Step 6 begins when the patient inhales with valves 413 and 415 closed and 410 and 411 in the opposite state shown. The vacuum pump 420 starts immediately drawing air from ambient at port 430, through valve 411 and into the inlet of pump 420. That air is pumped through vacuum pump 420 and back through the other path in valve 411, through valve 410 and into the feed end of column 400. The pressure in column 400 is slightly raised in this way until it is sufficient to open check valve 417 and vent product oxygen out of port 431 to the nose cannula worn by the patient. Vacuum pump 420 is controlled in its flow rate and pumping duration to deliver a pulse of oxygen rich gas to the patient that is shaped in its flow rate and duration.

The steps outlined above are performed on column 400 or on 401 selected by the state of valve 410. This toggles from one column to the other every patient inhalation. Some cycle steps are overlapped and performed concurrently on the two columns to save cycle time and to be able to keep up with a rapid breathing rate.

The portable oxygen concentrator using this separation apparatus delivers oxygen to a patient in pulses that are synchronized with the beginning of their breath inhalation. This eliminates the waste of oxygen and associated energy that occurs during a patient's exhalation or breath hold. The separation cycle is well suited to that requirement. In one embodiment, the cycle is stopped and held at the end of each pressurization step until the patient's inhalation began. The second half of the feed step is then rapidly completed producing product oxygen within about 0.4 seconds with a small pressure rise above 1 atmosphere (101 kPa), just enough to pressurize the product oxygen to induce flow through a short breathing cannula. While the patient continues through the breathing cycle sequence of inhalation, exhalation, and breath hold, the next separation cycle steps are being performed, through pressurization, and again held waiting for the next inhalation. There is no need for any added oxygen storage or dispensing components. As shown in FIG. 4, the oxygen concentrator does not contain a separate storage structure, reservoir, or accumulator for the separated gas. Oxygen is separated and dispensed directly from the separation column, in real time, through the cannula to the patient. All activity involved in the separation cycle, including operation of the pump, is halted while waiting for the next inhalation. This provides additional energy savings, important in the portable application.

The oxygen flow pulses need to be variable in volume to match the specific needs of each patient. This separation cycle is suited to that requirement. The amount of oxygen produced in one feed step of the cycle is variable in accordance with the end vacuum level. Lower end evacuate pressures produced larger volumes of oxygen during each feed. Higher end vacuums produced smaller volumes while the oxygen pressurization of the columns from the LIFO buffer maintained adequate oxygen purity by always keeping the product end of the columns at a low nitrogen partial pressure. Higher end evacuate pressures require less pump energy and allowed faster evacuations and a greater fraction of time spent with the cycle on hold. This produces energy savings when reduced oxygen volumes are selected.

Minimizing the work load on the pump in these ways reduces the peak pumping requirements and therefore generally reduces the size and weight of the vacuum pump. Using an adsorbent with a steep nitrogen isotherm and cycling it below 1 atmosphere where it is the steepest allows adsorbent columns with less size and weight for a given nitrogen capacity. Smaller than normal amounts of oxygen are lost to the waste stream during the evacuate step due in combination to the low oxygen adsorption capacity of the adsorbent in the vacuum range, the cycle that passes little oxygen from the product end to the waste stream of the column during evacuate, and little oxygen left in the column at the end of feed due to operation near breakthrough of the mass transfer zone. This all contributes to a high oxygen recovery rate for the cycle and therefore less waste stream flow created for a given oxygen product flow. Smaller scale pump, valves, and connecting components can be used to handle this reduced evacuated waste stream.

A portable medical oxygen concentrator using this separation apparatus with a custom designed high efficiency vacuum pump separates oxygen while consuming 12.7 watts per liter per minute of 88% pure oxygen. The portable concentrator weighs 2.5 pounds per liter per minute fully packaged. For comparison, the Invacare concentrator that was tested and utilizes the Skarstrom pressure swing cycle consumed 70 watts per liter per minute and weighs 10.4 pounds per liter per minute.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A delivery system for oxygen separated from ambient air comprising:
    a separator comprising:
    at least one separation column, the at least one separation column containing an inlet at a first end and an outlet at a second end;
    a last in/first out (LIFO) buffer column having a single inlet at a first end and having an adsorbent with a high capacity for nitrogen adsorption; wherein the LIFO buffer column is configured to receive through the single inlet a first stream of high purity oxygen from the outlet of the at least one separation column, reorder the single stream, and feed a reordered stream of high purity oxygen through the single inlet and to the at least one separation column;
    a vacuum pump;
    a valve system that connects the vacuum pump with the at least one separation column;
    wherein the vacuum pump is connected to the valve system to remove gas from the at least one separation column by enabling a flow path from the at least one separation column to a pump inlet of the vacuum pump, and to transfer a gas into the at least one separation column by enabling a different flow path from a pump outlet to the at least one separation column;
    a nose cannula;
    wherein the oxygen separator separates oxygen from air in discrete pulses and supplies oxygen through a check valve to the nose cannula directly from the at least one separation column in response to inhalation by a person through the nose cannula.

2. The delivery system of claim 1 wherein the separator separates oxygen from ambient air at a pressure of less than 1 atm.

3. The delivery system of claim 2 wherein the system does not contain a separate storage structure, reservoir, or accumulator for the separated gas.

4. The delivery system of claim 2 wherein the valve system further connects the at least one separation column with the LIFO buffer column.

5. The delivery system of claim 2 wherein the vacuum pump has a controllable variable pumping rate capable of producing a pulse of gas flow in 0.4 seconds from a fully stopped state of the separator.

6. A delivery system for oxygen separated from ambient air comprising:
    a separator comprising:
    at least one separation column, the at least one separation column containing a first port at a first end and a second port at a second end;
    a buffer column having a third port at a first end, and having an adsorbent with a high capacity for nitrogen adsorption;
    a vacuum pump;
    a valve system that connects the vacuum pump with the at least one separation column, and connects the at least one separation column and buffer column;
    wherein the vacuum pump is connected to the valve system to remove gas from the at least one separation column by enabling a flow path from the at least one separation column to a pump inlet of the vacuum pump, and to transfer a gas into the at least one separation column by enabling a different flow path from a pump outlet to the at least one separation column;
    a cannula;
    wherein the oxygen separator separates oxygen from air in discrete pulses and supplies oxygen through a check valve to the cannula directly from the at least one separation column in response to inhalation by a person through the cannula; and
    wherein the oxygen separator utilizes the buffer column containing the third port at the first end thereof for controlling flow in and out of the buffer column, functioning as a last in/first out (LIFO) buffer for the purity of separated gas flowing in and out of the at least one separation column with the buffer column reordering the flow in and out of the buffer column.

7. The delivery system of claim 6, wherein the LIFO buffer orders and stores a first stream of the separated gas in declining oxygen purity toward an end of the first stream, and returns the separated gas in a second stream increasing in oxygen purity toward an end of the second stream.

8. The delivery system of claim 7 wherein the vacuum pump has a controllable variable pumping rate capable of producing a pulse of gas flow in 0.4 seconds from a fully stopped state of the separator.

9. The delivery system of claim 6 wherein the separator separates oxygen from ambient air at a pressure of less than 1 atm.

10. The delivery system of claim 6 wherein the system does not contain a separate storage structure, reservoir, or accumulator for the separated gas.

\* \* \* \* \*